(12) United States Patent
Johnson et al.

(10) Patent No.: US 10,464,289 B2
(45) Date of Patent: Nov. 5, 2019

(54) PEELABLE FILM FOR PACKAGING

(71) Applicant: Berry Plastics Corporation, Evansville, IN (US)

(72) Inventors: Eric Johnson, Brazil, IN (US); Paul Z Wolak, Indianapolis, IN (US)

(73) Assignee: Berry Plastics Corporation, Evansville, IN (US)

( * ) Notice: Subject to any disclaimer, the term of this patent is extended or adjusted under 35 U.S.C. 154(b) by 0 days.

(21) Appl. No.: 13/892,147

(22) Filed: May 10, 2013

(65) Prior Publication Data

US 2013/0299373 A1 Nov. 14, 2013

Related U.S. Application Data

(60) Provisional application No. 61/645,410, filed on May 10, 2012.

(51) Int. Cl.
| | |
|---|---|
| *B32B 7/06* | (2019.01) |
| *A61M 5/00* | (2006.01) |
| *B32B 27/10* | (2006.01) |
| *B32B 27/18* | (2006.01) |
| *B32B 27/32* | (2006.01) |
| *A61B 50/00* | (2016.01) |
| *A61B 50/30* | (2016.01) |
| *A61B 17/3201* | (2006.01) |
| *A61B 17/00* | (2006.01) |

(52) U.S. Cl.
CPC ............... *B32B 7/06* (2013.01); *A61B 50/00* (2016.02); *A61B 50/30* (2016.02); *A61M 5/002* (2013.01); *B32B 27/10* (2013.01); *B32B 27/18* (2013.01); *B32B 27/32* (2013.01); *A61B 17/3201* (2013.01); *A61B 2017/00526* (2013.01); *A61B 2050/314* (2016.02); *B32B 2270/00* (2013.01); *B32B 2307/31* (2013.01); *B32B 2307/748* (2013.01); *B32B 2439/80* (2013.01); *B32B 2553/00* (2013.01); *Y10T 428/269* (2015.01)

(58) Field of Classification Search
CPC ........... B32B 7/06; B32B 27/10; B32B 27/18; B32B 27/32; B32B 2553/00; A61B 50/00; Y10T 428/269
See application file for complete search history.

(56) References Cited

U.S. PATENT DOCUMENTS

| | | | |
|---|---|---|---|
| 3,891,089 A | 6/1975 | Goodwin et al. | |
| 4,367,256 A | 1/1983 | Biel | |
| 5,209,884 A * | 5/1993 | Wood, Jr. ......................... | 264/41 |

(Continued)

FOREIGN PATENT DOCUMENTS

| | | |
|---|---|---|
| EP | 1312470 A1 | 5/2003 |
| JP | 05245067 | 10/1993 |

(Continued)

OTHER PUBLICATIONS https://books.google.com/books?id=II3_CgAAQBAJ&pg=PA39&dq=polybutene-1&hl=en&sa=X&ved=0ahUKEwj7gfTdt7LQAhUK6yYKHcJIDfwQ6AEINDAE#v=onepage&q=polybutene-1&f=false.*

(Continued)

*Primary Examiner* — Samir Shah
(74) *Attorney, Agent, or Firm* — Barnes & Thornburg LLP

(57) ABSTRACT

A film is mated with a paper to form a space therebetween. The film is made of plastics material. Separation of the paper from the film can provide access to an article stored in the space provided between the paper and the film.

6 Claims, 9 Drawing Sheets

(56) References Cited

U.S. PATENT DOCUMENTS

| | | | |
|---|---|---|---|
| 6,189,694 | B1 | 2/2001 | Weiss et al. |
| 6,256,966 | B1 | 6/2001 | Braun et al. |
| 6,280,085 | B1 | 8/2001 | Beer |
| 6,309,756 | B1 * | 10/2001 | Alder .................. B32B 27/32 428/319.9 |
| RE37,171 | E | 5/2011 | Busche et al. |
| 2002/0122952 | A1 * | 9/2002 | Delisio ................ B32B 27/32 428/516 |
| 2005/0129811 | A1 * | 6/2005 | Kraimer et al. .............. 426/106 |
| 2005/0192414 | A1 * | 9/2005 | Donck ................ B01J 19/2415 526/64 |
| 2006/0147738 | A1 | 7/2006 | Longmore |
| 2007/0083009 | A1 * | 4/2007 | Chai .............. C09D 123/0815 525/240 |
| 2008/0286547 | A1 * | 11/2008 | Hubbard et al. ............. 428/220 |
| 2008/0299364 | A1 * | 12/2008 | Nilsen ................. B32B 27/32 428/213 |
| 2010/0129632 | A1 | 5/2010 | Eichbauer et al. |
| 2012/0100356 | A1 * | 4/2012 | Ohlsson ............... B32B 27/20 428/213 |

FOREIGN PATENT DOCUMENTS

| | | |
|---|---|---|
| JP | 5254067 A | 10/1993 |
| JP | 10129720 A | 5/1998 |
| JP | 2002128128 A | 5/2002 |
| JP | 2003237816 | 8/2003 |
| JP | 2003237816 A | 8/2003 |
| JP | 2003237816 A1 | 8/2003 |
| JP | 2006256144 | 9/2006 |
| JP | 2006256144 A | 9/2006 |
| JP | 2011079584 A | 4/2011 |
| JP | 2015006771 A | 1/2015 |
| WO | 2011012649 | 2/2011 |

OTHER PUBLICATIONS

PCT international Search Report and Written Opinion completed by the ISA/US dated Sep. 25, 2013 and issued in connection with PCT/US2013/040630.

English language summary of Chinese Office Action for Chinese Application Serial No. 201380030911.2, dated Jan. 6, 2016, 19 pages.

Japanese Office Action for Japanese App. No. 2015-511776 dated May 9, 2017, BP-380 Jp II, 12 pages.

Dominican Republic Office Action for Dominican Republic App. No. P2014-0246, dated Apr. 19, 2017, 6 pages.

Danafilms, Blow Film Glossary, Technical Terms, http://danafilms.com/techtermsglossary.htm, 3 pages.

Japanese Office Action for Japanese App. No. 2015-511776 dated Jan. 9, 2018, BP-380 JP II, 5pages.

Malaysian Office Action for Malaysian Patent App. No. PI2014703314 dated Jan. 15, 2018, BP-380 MY II, 3 pages.

Notice of Dismissal of Request for Reconsideration of the Decision of Rejection for Japanese App. No. 2015-511776 dated Jul. 2, 2018, 4 pages, machine translation provided.

Dominican Republic Office Action for Dominican Republic App. No. P2014-0246, dated Apr. 3, 2018, 4 pages, (No English translation available, only a summary).

Mexican Office Action for Mexican Patent App. No. MX/a/2014/013610 dated May 29, 2018, BP-380 MX II, 9 pages.

European Office Action for European Patent App. No. 13787056.4 dated Nov. 22, 2018, BP-380 EP II, 6 pages.

Extended European Search Report for European App. No. 13787056A dated Aug. 26, 2015, BP-380 EP II, 9 pages.

Notification of Reason for Refusal of Japanese App. No. 2015-511776 dated Jan. 8, 2019, BP-380 JP II, 10 pages.

Dominican Republic Office Action for Dominican Republic App. No. P2014-0246, received Jan. 24, 2019, BP-380 DO II, 5 pages, (No English translation available, only a summary).

Korean Office Action for Korean App. No. 10-2014-7034240 dated Feb. 14, 2019, BP-380 KR II, 7 pages pages.

Canadian Examiner's Report for Canadian App. No. 2,871,935 dated Feb. 8, 2019, BP-380 CA II, 4 pages.

First Examination Report for Indian Patent App. No. 9642/DELNP/2014 dated Feb. 26, 2019, BP-380 IN II, 6 pages.

Japanese Office Action for Japanese App. No. 2018-089089 dated Jul. 9, 2019, BP-380 JP-DIV1 II, 7 pages.

Dominican Republic Resolution for Dominican Republic App. No. P2014-0246, dated Aug. 13, 2019, BP-380 DO I, 23 pages, (No English translation available, only a summary).

* cited by examiner

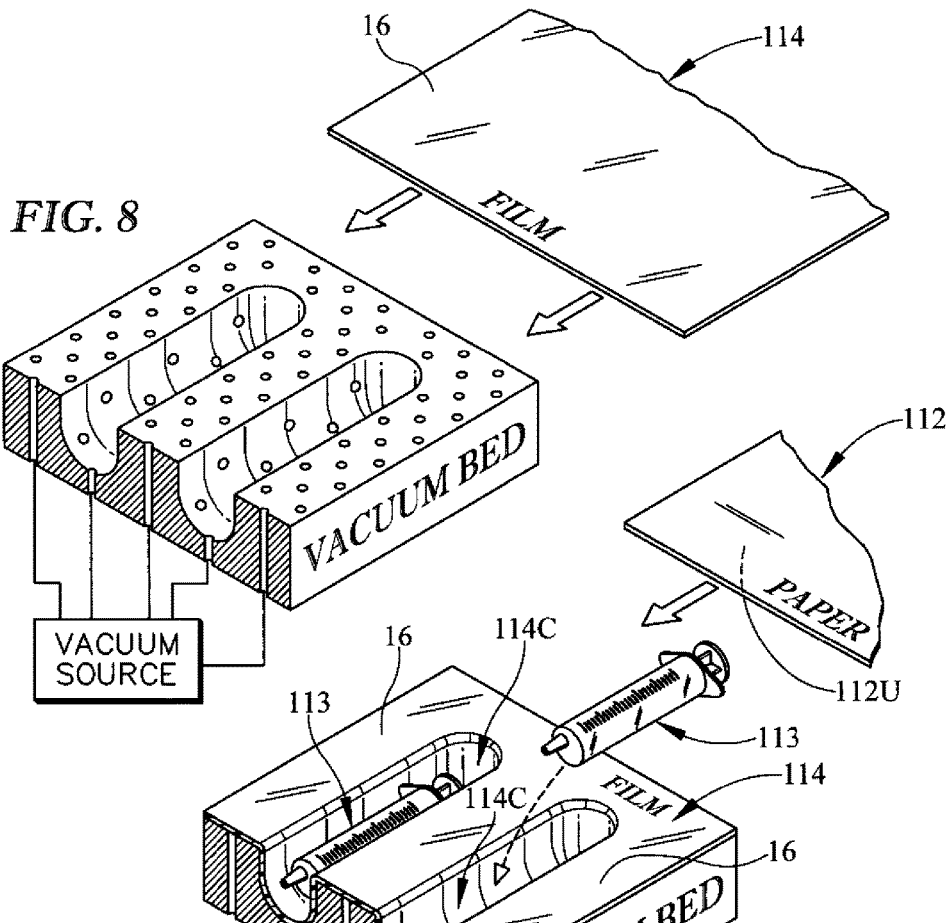
FIG. 8
FIG. 9
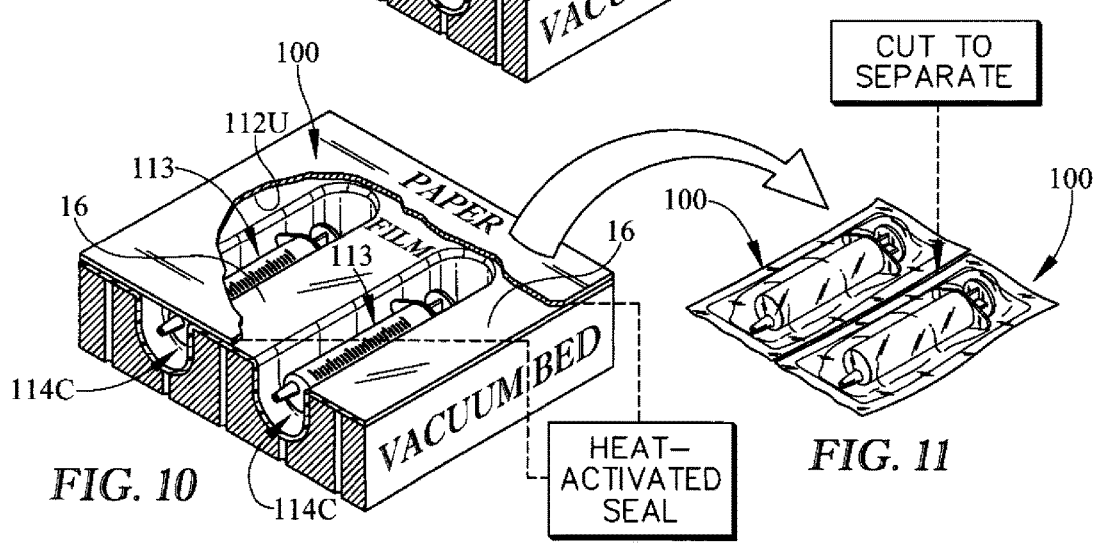
FIG. 10
FIG. 11

PEELABLE FILM FOR PACKAGING

PRIORITY CLAIM

This application claims priority under 35 U.S.C. § 119(e) to U.S. Provisional Application Ser. No. 61/645,410, filed May 10, 2012, which is expressly incorporated by reference herein.

BACKGROUND

The present disclosure relates to films that are mated to paper, and particularly to films for use in packaging. More particularly, the present disclosure relates to sterilizable packaging for medical devices.

SUMMARY

According to the present disclosure, a film is provided for use in a package. In illustrative embodiments, the film is mated to a substrate (sometimes called lid-stock) to form an article-receiving space therebetween and establish a sterilizable package. In illustrative embodiments, the substrate is made of paper, another film, or a container.

In illustrative embodiments, the film is a blown co-extruded film or a cast film having multiple layers including a skin layer that is bonded to the substrate to form the article-receiving space. The substrate is a paper having an uncoated sealant side and paper fibers. The skin layer comprises a selected blend of polymers and other materials exhibiting selected adhesion properties that cooperate to provide peelable skin means for bonding the film when exposed to heat to the uncoated sealant side of the paper to establish the article-receiving space and for releasing the film from the uncoated sealant side of the paper in response to application of an external peeling force to either the film or the paper without separating paper fibers from the uncoated sealant side of the paper and discharging paper fibers into the article-receiving space so that the uncoated sealant side of the paper remains substantially intact during separation of the film from the uncoated sealant side of the paper.

In illustrative embodiments, the skin layer of the film comprises polyethylene in the 6 MI range (Melt Index) in combination with about 40% polybutene-1 and suitable slip and anti-block components. This blend cooperates to provide an easy-to-peel film layer with suitable bond strength to an uncoated sealant side of a paper substrate. In illustrative embodiments, the skin layer is thin (e.g., as little as about 5-6% to as much as about 20% depending on the total thickness of the peelable film) and in one example in accordance with the present disclosure is about 10% of the thickness of the film. It is within the scope of this disclosure to provide a co-extruded film having a skin layer that bonds to and releases from a wide variety of substrates including an uncoated sealant side of a paper substrate.

Additional features of the present disclosure will become apparent to those skilled in the art upon consideration of illustrative embodiments exemplifying the best mode of carrying out the disclosure as presently perceived.

BRIEF DESCRIPTION OF THE DRAWINGS

The detailed description particularly refers to the accompanying figures in which:

FIGS. 8-11 show an illustrative process for forming the package shown in FIGS. 5-7;

FIG. 8 is a diagrammatic view showing movement of a multilayer film which is pre-heated and then vacuum-drawn and/or pressure-pushed into a cavity to cause the skin layer to face upwardly away from the cavity as suggested in FIG. 9;

FIG. 9 is a view similar to FIG. 8 suggesting that the multilayer film is thermo-formed on the vacuum bed to form two article-storage channels arranged to lie in side-by-side relation to one another, a first syringe is placed in one of the article-storage channels and a second syringe is about to be placed in the other article-storage channel, and paper having a downwardly facing uncoated sealant side is moved toward the thermoformed film and the two syringes;

FIG. 10 is a view similar to FIGS. 8 and 9, with portions broken away, showing that the downwardly facing uncoated sealant side of the paper has been mated to the upwardly facing skin layer of the film by means of a heat-activated seal;

FIG. 11 is a reduced-size perspective view of two packages discharged from the vacuum bed of FIG. 10 and inverted so that the paper substrate is below the film.

DETAILED DESCRIPTION

Figure 1:
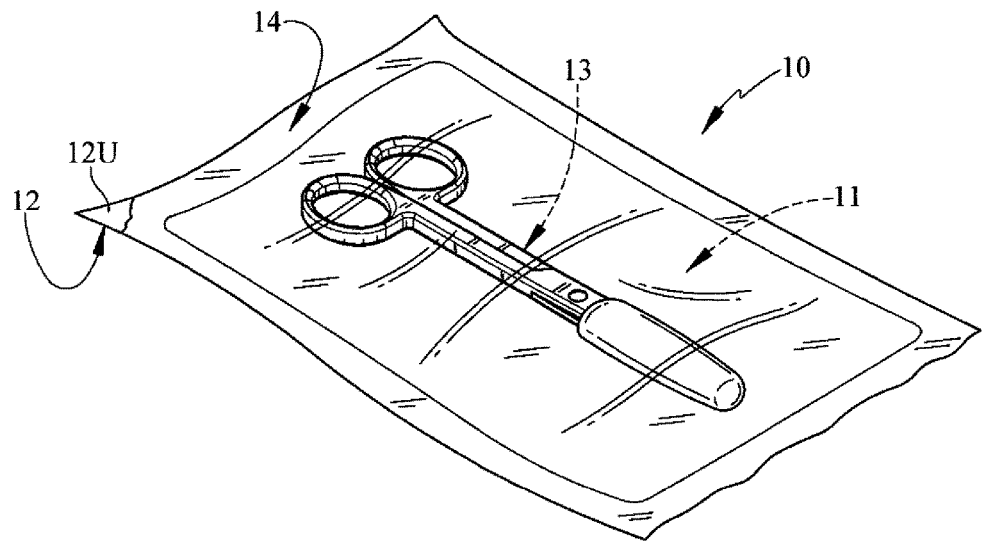
FIG. 1 is a perspective view of a package in accordance with a first embodiment of the present disclosure formed to include an article-receiving space containing a scissors, with a portion broken away to reveal an upwardly facing uncoated sealant side of a paper substrate.
Figure 2:
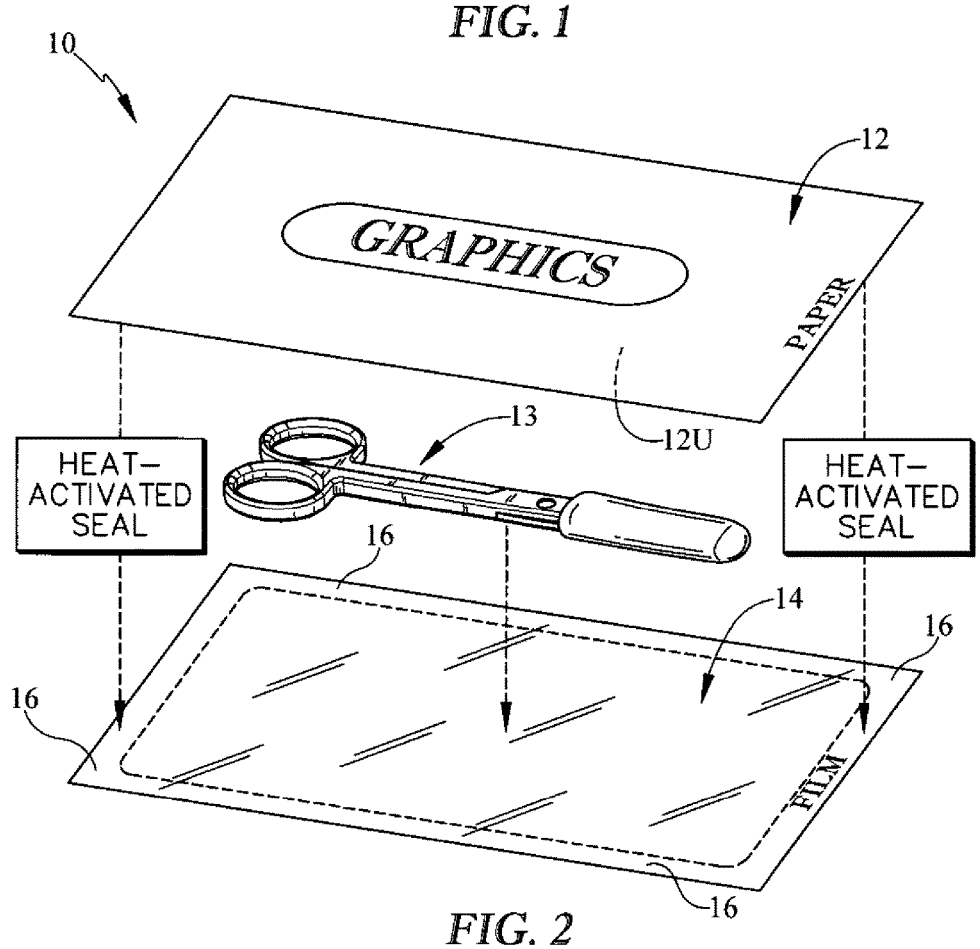
FIG. 2 is an exploded perspective assembly view showing that the package of FIG. 1 includes (from top to bottom) a substrate (topweb) made of paper having an uncoated sealant side and bearing printed graphics material, a scissors, and a film (web) including a skin layer facing upwardly toward the downwardy facing uncoated sealant side of the paper and suggesting that the skin layer mates with the uncoated sealant side of the paper by means of a heat-activated seal to bond the film to the uncoated sealant side of the paper and form an article-receiving space therebetween containing the scissors.

A package 10 in accordance with a first embodiment of the present disclosure is shown in FIG. 1 and includes a substrate 12 comprising paper having an uncoated sealant side 12U and a multilayer film 14 comprising a skin layer 16 adapted to be bonded to uncoated sealant side 12U of paper 12 to form an article-receiving space 11 containing an article 13 (e.g., scissors) as suggested in FIG. 2. To access scissors 13, a technician can peel back paper 12 as suggested in FIG. 3 to release uncoated sealant side 12U of paper 12 from skin layer 16 of film 14 without separating paper fibers from uncoated sealant side 12U of paper 12 and discharging those paper fibers into the article-receiving space 11 so that no fiber tear is present. A package 100 in accordance with a second embodiment of the present disclosure is suggested in FIGS. 5-12.

Figure 3:
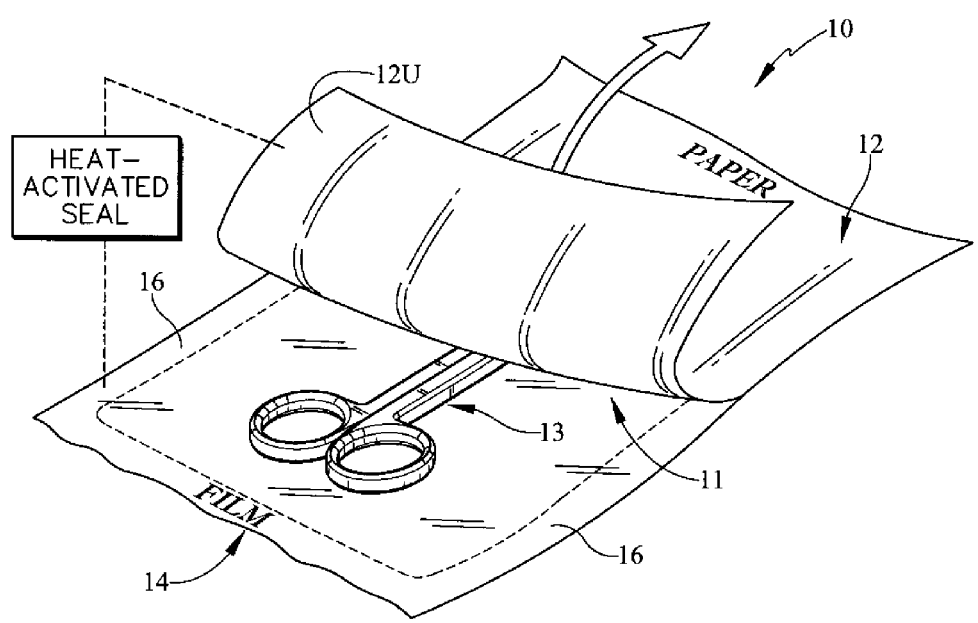
FIG. 3 is a perspective view of the package of FIGS. 1 and 2 showing that an external peeling force is being applied, for example, to the paper to release the skin layer of the multilayer film from a bonded connection to the uncoated sealant side of the paper without separating paper fibers from the uncoated sealant side of the paper and discharging paper fibers into the article-receiving space formed between the film and the uncoated sealant side of the paper so that the uncoated sealant side of the paper remains substantially intact during separation of the paper from the film.

A package 10 includes paper 12 and film 14 as suggested in FIGS. 1-3. Paper 12 has an uncoated sealant side 12U comprising paper fibers. Film 14 includes a skin layer 16 configured to provide peelable skin means for bonding film 14 to uncoated sealant side 12U of paper 12 when exposed to heat to establish an article-receiving space 11 therebetween as suggested in FIGS. 1 and 2 and for releasing film 14 from uncoated sealant side 12U of paper 12 in response to application of an external peeling force to one of film 14 and paper 12 without separating paper fibers from uncoated sealant side 12U of paper 12 and discharging paper fibers into article-receiving space 11 so that uncoated sealant side 12U of paper 12 remains substantially intact during separation of film 14 from uncoated sealant side 12U of paper 12 as suggested in FIG. 3.

Blown co-extruded film is used herein to create a (forming) web that can be sealed directly to an uncoated sealant side of a paper with sufficient seal strength to survive packaging, sterilization, and distribution. Yet the package made in accordance with the present disclosure remains easy to open by the end user when the package contents are needed without any paper fiber shed by the uncoated sealant side of the paper to contact the package contents. Further, seals made in accordance with the present disclosure provide consistent peelability over a broad operating range on packaging machinery.

Film 14 is bonded to uncoated sealant side 12U of paper 12 or other suitable substrate using heat as suggested in FIG. 2 to trap an article such as scissors 13 in an article-receiving space 11 formed between film 14 and uncoated sealant side 12U of paper 12. Skin layer 16 of film 14 bonds directly to uncoated sealant side 12U of paper 12 to provide a hermetic seal therebetween and yet skin layer 16 separates very easily (i.e., unbonds) from uncoated sealant side 12U of paper 12 when paper 12 is peeled back as suggested in FIG. 3. Film 14 is a web that is heat-sealed to the uncoated sealant side 12U of paper topweb 12. Package 10 can be sterilized by exposure to high temperature, ethylene oxide gas, or radiation to cause a scissors 13 stored in package 10 also to be sterilized.

Skin layer 16 of film 14 is a composition in accordance with the present disclosure that releases easily from uncoated sealant side 12U of paper 12 in an unexpected manner to break the hermetic seal between uncoated sealant-side 12U of paper 12 and film 14 to access scissors 13 without separating paper fibers from uncoated sealant side 12U of paper 12 and discharging paper fibers into article-receiving space 11 where such fibers may contact scissors 13 as package 10 is being opened. Skin layer 16 is one of, for example, many layers included in a co-extruded multilayer film 14 in illustrative embodiments of the present disclosure. Examples of illustrative films in accordance with the present disclosure are included in FIGS. 4A-4C. It is therefore unnecessary to use an expensive coated paper as a substrate owing to the adhesion properties of skin layer 16 in film 14. Costly coatings are often applied to sealant sides of paper substrates to cause those paper substrates to adhere to a film web with a specific seal strength and to cause those paper substrates not to shed any paper fibers during separation of the film from the paper substrate or otherwise exhibit any signs of fiber tear. Films as disclosed herein can be made by many methods, including, but not limited to, blown film co-extrusion and cast film co-extrusion processes.

Film 14 is a blown coextruded film, illustratively a multilayer web with a skin layer 16 that is capable of forming a peelable hermetic seal to an uncoated sealant side 12U of paper topweb 12. The seal peels cleanly without pulling paper fibers from the uncoated sealant side 12U of paper 12 during seal opening in accordance with the present disclosure.

The present disclosure takes advantage of our discovery that a co-extruded multilayer film with a novel skin layer is capable of forming a peelable hermetic seal to an uncoated sealant side of a paper substrate, which seal provides greater than 300 g/in bond strength as measured by ASTM F88 (preferably greater than 450 g/in bond strength). This seal peels cleanly without pulling paper fibers from the paper substrate during seal opening (as determined, for example, by visual inspection of the film after seal opening).

Figure 4A:
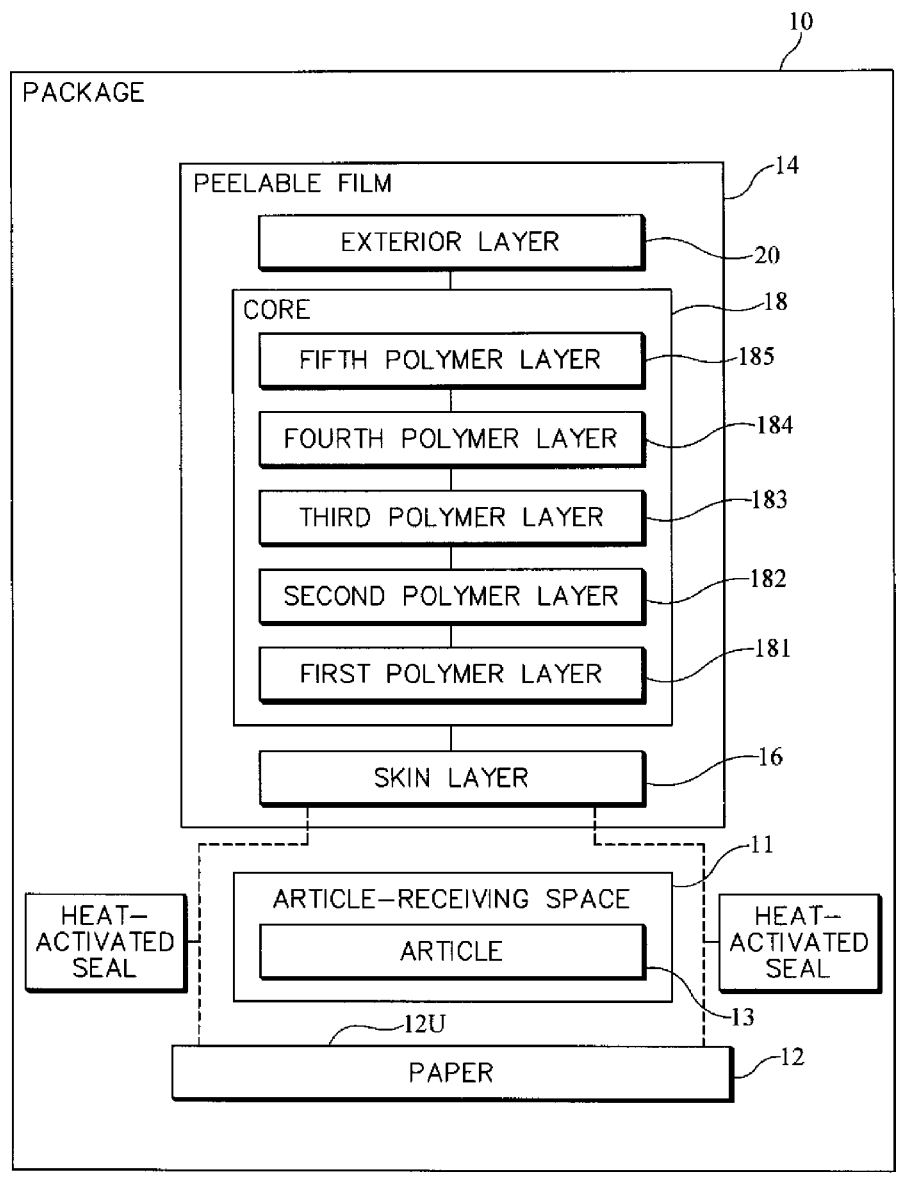
FIG. 4A is a diagrammatic view of a package comprising a paper substrate and a companion multilayer film in accordance with a first embodiment of the present disclosure and suggesting that a heat-activated seal is created between a skin layer of a peelable film and an upwardly facing uncoated sealant side of a paper substrate.

In an illustrative first embodiment shown in FIG. 4A, a package 10 comprises paper substrate 12 having an uncoated sealant side 12U, a peelable co-extruded multilayer film 14, and an article-receiving space 11, which space is occupied by article 13 where article 13 is interposed and arranged to contact paper substrate 12 and peelable film 14. Peelable film 14 comprises skin layer 16, core 18, and exterior layer 20, where core 18 is interposed and in contact with skin layer 16 and exterior layer 20. Skin layer 16 of peelable film 14 is bonded to uncoated sealant side 12U of paper substrate 12 by means of a heat-activated hermetic seal. Core 18 comprises, in series, a first polymer layer 181, a second polymer layer 182, a third polymer layer 183, a fourth polymer layer, and a fifth polymer layer 185.

Figure 4B:
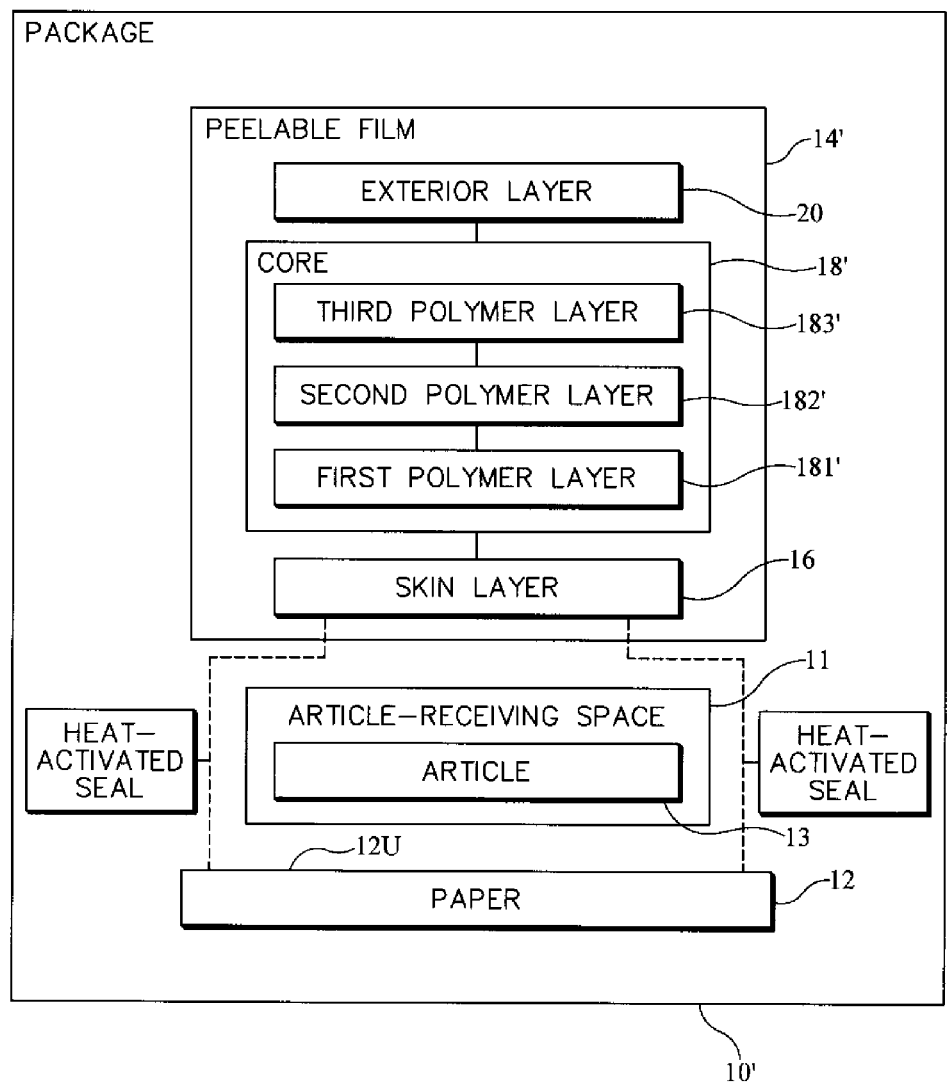
FIG. 4B is a diagrammatic view of a package comprising a paper substrate and a companion multilayer film in accordance with a second embodiment of the present disclosure.

In an illustrative second embodiment shown in FIG. 4B, a package 10' comprises a paper substrate 12 having an uncoated sealant side 12U, a peelable co-extruded multilayer film 14', and an article-receiving space 11, which space is occupied by article 13 (e.g., scissors or a syringe) where article 13 is interposed and arranged to contact paper substrate 12 and peelable film 14'. Peelable film 14' comprises skin layer 16, core 18', and exterior layer 20, where core 18' is interposed and in contact with skin layer 16 and exterior layer 20. Skin layer 16 of peelable film 14' is bonded to uncoated sealant side 12U of paper substrate 12 by means of a heat-activated hermetic seal. Core 18' comprises a first polymer layer 181', a second polymer layer 182', and a third polymer layer 183'.

Figure 4C:
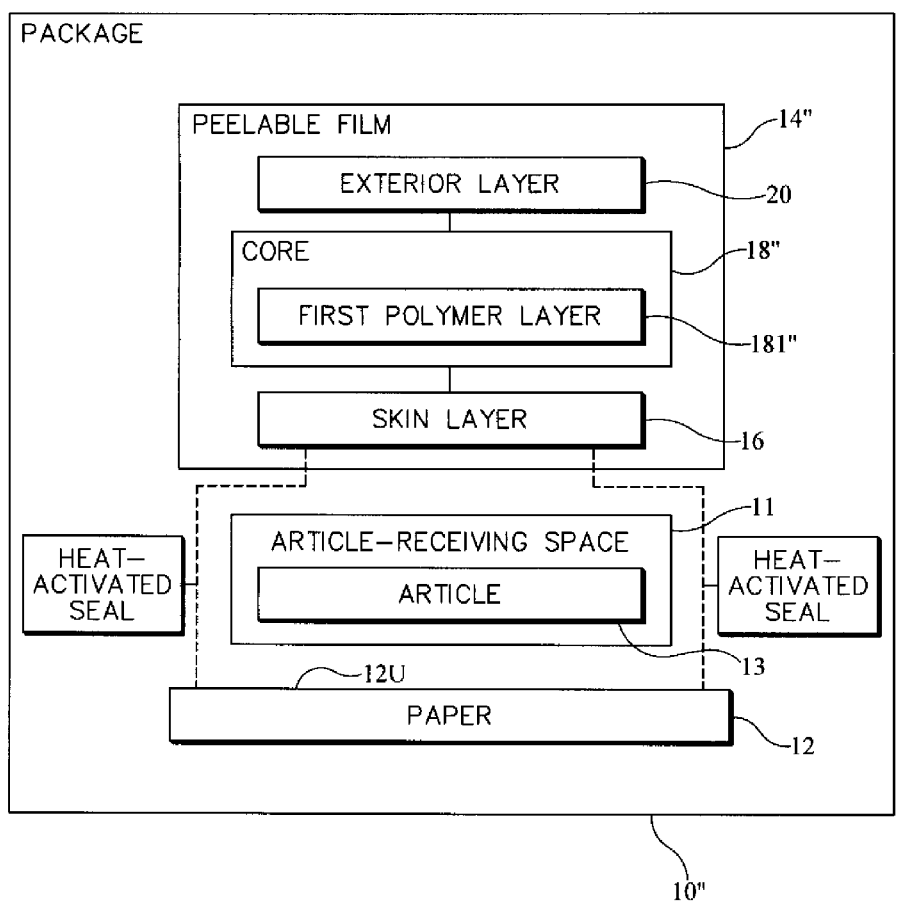
FIG. 4C is a diagrammatic view of a package comprising a paper substrate and a companion multilayer film in accordance with a third embodiment of the present disclosure.

In an illustrative third embodiment shown in FIG. 4C, a package 10" comprises paper substrate 12 having an uncoated sealant side 12U, a peelable co-extruded multilayer film 14", and an article-receiving space 11, which space is occupied by article 13 (e.g., scissors or a syringe) where article 13 is interposed and arranged to contact paper substrate 12 and peelable film 14". Peelable film 14" comprises skin layer 16, core 18", and exterior layer 20, where core 18" is interposed and in contact with skin layer 16 and exterior layer 20. Skin layer 16 of peelable film 14" is bonded to uncoated sealant side 12U of paper substrate 12 by means of a heat-activated hermetic seal. Core 18" comprises a first (single) polymer layer 181".

Package 10 includes a substrate 10 and a multilayer film 14 as suggested in FIGS. 1-3 and 4A. Substrate 12 comprises a paper having an uncoated sealant side 12U and including paper fibers. Film 14 is coupled to substrate 12 to form an article-receiving space 11 located therebetween and adapted to receive an article 13 therein. The multilayer film 14 including an exterior layer 20 and a skin layer 16 interposed between exterior layer 20 and uncoated sealant side 12U of paper included in substrate 12 as suggested in FIG. 4A. Skin layer 16 is configured as suggested I FIGS. 1-4A to provide heat-activated seal means for bonding to uncoated sealant side 12U of paper included in substrate 12 during exposure of skin layer 16 to heat in excess of a predetermined temperature to trap an article 13 that is present in article-receiving space 11 between skin layer 16 and uncoated sealant side 12U of paper 12 to cause uncoated sealant side 12U of paper 12 to bond to skin layer 16 to establish a hermetic seal therebetween that surrounds article-receiving space 11 to retain an article 13 present in article-receiving space 11 in a hermetically sealed chamber as suggested in FIGS. 1 and 2 and for unbonding from uncoated sealant side 12U of paper 12 included in substrate 12 in response to application of an external paper-peeling force to paper 12 to break bonds between uncoated sealant side 12U of paper 12 and skin layer 16 as uncoated sealant side 12U of paper 12 is peeled away from skin layer 16 without separating paper fibers from uncoated sealant side 12U of paper 12 and discharging those paper fibers into article-receiving space 11 so that article-receiving space 11 and any article 13 in article-receiving space 11 are uncontaminated by paper fibers associated with uncoated sealant side 12U of paper 12 when a consumer separates at least a portion of uncoated sealant side 12U of paper 12 from skin layer 16 of the multilayer film 14 to gain access to an article 13 in article-receiving space 11 as suggested in FIG. 3.

One aspect of the present disclosure is that the interposed skin layer 16 is relatively thin, representing a minor amount (e.g., as little as about 5-6% to as much as about 20%) of the thickness of co-extruded multilayer film 14/14'/14", but the effect of the skin layer on the properties of the film is in no way diminutive. In other words, the dimensional contribution of skin layer 16 may be small, but the consequence of its inclusion leads to a significant improvement in the peelability properties of the multilayer film. In this respect, the interposed skin layer's thickness contributes only slightly to the total thickness of the film, but substantially to the film's overall properties. While not being limited to any particular theory, it is believed that the combination of thickness (e.g., as little as about 5-6% to as much as about 20% depending on the total thickness of the multilayer peelable film), polymer melt index (in the range of about 3 to about 10), and polyolefin content (e.g., about 40% polybutene-1) of the skin layer in combination with suitable slip and anti-block components contribute substantially to the peelability characteristics described herein. In addition to polybutene-1, other poly-alpha olefins that can impart peelability are also contemplated to be within the scope of the present disclosure.

As used herein, the term core is a layer configuration of one or more layers of polyolefins or plastics. The term core is used even for a single-layer configuration. As used herein, the term layer is a planar arrangement of polyolefins or plastics which may or may not include multiple polyolefinic components. The term layer includes continuous planar arrangements, but is not limited to such arrangements. The term layer also includes discontinuous planar arrangements, for example, meshes, porous sheets, perforated sheets, and scrims.

Melt Index. As used herein, the term Melt Index (MI) is a measure of the ease of flow of a polymeric composition. MI equals the mass of polymer in grams flowing in 10 minutes through a capillary of specific diameter and length by an applied pressure. ASTM D-1238-00 refers to the standard test method for determining the melt index. MI is an indirect measure of molecular weight; a high melt index typically corresponds to low molecular weight. Furthermore, MI is a measure of the ability of the polymer composition to flow under pressure in its melted form. MI may be considered as inversely proportional to viscosity, but the viscosity is also dependent on the applied force.

Molecular Weight. Many analytical techniques are available for the determination of the MW and MWD. One such approach is described in ASTM D 4001-93 (2006) which refers to the standard test method for determination of weight-average molecular weight of polymers by light scattering. Gel permeation chromatography (GPC) can provide information on the MW as well as the MWD. Another technique which may be used to determine the properties of one or more of the polymer compositions described herein includes temperature rising elution fractionation (TREF). Furthermore, gel permeation chromatography (GPC) can be coupled with TREF to obtain other properties of a particular polymeric composition.

Density. Density values refer to those obtained according to ASTM D 1505-98, which is the standard test method for density of plastics by the density-gradient technique.

Branching. The extent to which a polymer is branched and the length of those branches may be determined by, for example, C-13 NMR, GPC, temperature rising elution fractionation (TREF), and Crystallization analysis fractionation (Crystaf). Furthermore, rheological properties may be used to compare relative amounts of short and long chain branching. For example, relaxation time reflects the time taken for the polymer chains to relax after deformation in a molten condition. Another way to analyze the branching is through linear thermal shrinkage. A polymer in the form of a film or sheeting may be tested according to ASTM D 2732-96.

ASTM D 2732 refers to the standard test method for unrestrained linear thermal shrinkage. Unrestrained linear thermal shrinkage, otherwise known as free shrink, refers to the irreversible and rapid reduction in linear dimension in a specified direction occurring in film subjected to elevated temperatures under conditions where nil or negligible restraint to inhibit shrinkage is present.

Short chain branching (SCB), as used herein, is branching of less than approximately 40 carbon atoms. One aspect of the present disclosure is the SCB may interfere with the formation of the microcrystalline structures. As used herein, long chain branching (LCB) is branching with lengths longer than the average critical entanglement distance of a linear polymer chain. For example, long chain branching includes branching with chain lengths greater than 40 carbon atoms. Another aspect of the present disclosure is that a substantially linear polyethylene includes substantial SCB but substantially no LCB. Accordingly, substantially linear polyethylene may be referred to as substantially short chain branched polyethylene.

As used herein, substantially no long chain branching is defined as a LCB density of less than about 0.01 long chain branch points per 1000 main chain carbons. As used herein, some long chain branching is defined as a LCB density of about 0.01 to about 0.2 long chain branch points per 1000 main chain carbons. As used herein, substantial long chain branching is used to describe polymers having greater than 0.2 long chain branch points per 1000 main chain carbons.

ASTM standard test methods incorporated by reference. Reference is made to each ASTM standard test methods described herein, which ASTM standard test methods are hereby incorporated by reference herein, for disclosure relating to the methods for testing polymeric compositions and films made thereof.

Analytical Limitations. Another aspect of the present disclosure is that adjacent layers may be comprised of compositions which are substantially indistinguishable through analytical techniques. This aspect of the present disclosure results in multilayer films which may have more layers than analytically perceivable. In one aspect, the present disclosure may involve introducing layers adjacent to each other which have very similar chemical and/or physical properties. The similarity of chemical and/or physical properties between the layers combined with the diminutive layer thickness may result in the number of layers perceived through analytical techniques being lower than the actual number of layers present.

cPE. As used herein, the term catalyzed polyethylene (cPE) is used generally to describe a copolymer of ethylene and an alpha olefin comonomer made through a catalyzed reaction (e.g., through a Ziegler-Natta, Philips, metallocene, or other single site catalyzed reactions). cPE includes polymers made through non-metallocene or post-metallocene catalyzed reactions resulting in a copolymer of ethylene and an alpha olefin copolymer. cPE includes copolymers made with various alpha olefin monomers including 1-butene, 3-methyl-1-butene, 3-methyl-1-pentene, 1-hexene, 4-methyl-1-pentene, 3-methyl-1-hexene, 1-octene or 1-decene. In one embodiment, the cPE is a copolymer of ethylene and one selected from the group of 1-hexene and 1-octene. In another embodiment, the cPE is a copolymer of ethylene and 1-octene.

In illustrative embodiments, the alpha olefin comonomer is selected from the group consisting of 1-butene, 1-hexene, and 1-octene. The alpha olefin comonomer may be incorporated from about 1% to about 20% by weight of the total weight of the polymer, preferably from about 1% to about 10% by weight of the total weight of the polymer. In one embodiment the alpha olefin comonomer is incorporated at a percentage of from about 6% to about 8%. In one embodiment, the alpha-olefin is butene incorporated at a percentage of between about 5% to about 15%. In another embodiment, the alpha-olefin is butene incorporated at a percentage of between about 5% to about 15%.

In illustrative embodiments, cPE has a MWD within the range of about 1 to about 6. In one embodiment, cPE has a MWD within the range of about 1.5 to about 5. In another embodiment, cPE has a MWD within the range of about 2 to about 4. In illustrative embodiments, the cPE has an average molecular weight from about 20,000 to about 500,000 g/mol, preferably from about 50,000 to about 200,000 g/mol.

VLDPE. As used herein, VLDPE is a cPE having a density of about 0.88 to about 0.92 g/cm$^3$ or from about 0.89 g/cm$^3$ to about 0.91 g/cm$^3$. It may be referred to as ultra low density polyethylene (ULDPE) or very low density polyethylene (VLDPE). VLDPE may have a MI of from about 0.5 to about 5 g/10 min, preferably from about 1 to about 4 g/10 min. For example, a VLDPE may have a density of about 0.91 g/cm$^3$ and a MI of about 3 g/10 min. Similarly, a VLDPE may have a density of about 0.90 g/cm$^3$ and a MI of about 4 g/10 min. A VLDPE having a density from about 0.90 to about 0.91 g/cm$^3$ and a MI of about 1 g/10 min may also be used. In one aspect, the characteristic density may have been achieved by copolymerizing ethylene with one of 1-butene, 1-hexene, 4-methyl-1-pentene, or 1-octene. In one embodiment, the VLDPE is a copolymer of ethylene and one comonomer selected from the group of 1-hexene and 1-octene. In another embodiment, the cPE is a VLDPE being a copolymer of ethylene and 1-octene, wherein copolymer has a mean comonomer percentage of about 10%.

LDPE. As used herein, low density polyethylene (LDPE) is defined as a polyethylene polymer with a density in the range of about 0.91 g/cm$^3$ to about 0.93 g/cm$^3$. LDPE may be polymerized through a free radical polymerization and has a high degree of short and long chain branching. The term LDPE is intended to include high pressure low density polyethylene (HPLDPE) polymerized through a high pressure free radical polymerization. For example, LDPE may be an ethylene homopolymer made using a free radical initiator at pressures from about 15,000 psi to about 50,000 psi and at temperature up to about 300° C. in a tubular or stirred reactor. According to this polymerization technique, numerous long chain branches may be formed along the length of the polymer. In one aspect, the LDPE may be characterized as having a single low melting point. For example, a 0.92 g/cm$^3$ density LDPE would typically have a melting point at about 112° C. In another aspect, LDPE may not pack into the crystal structures well. Therefore, LDPE may have a tendency to form amorphous solid structures. Accordingly, the intermolecular forces are weaker and the instantaneous-dipole induced-dipole attraction may be lower. Furthermore, LDPE has a lower tensile strength than HDPE but comparably greater ductility.

In illustrative embodiments, the film comprises LDPE having a MI of about 0.1 to about 20 g/10 min. In one embodiment, the film comprises LDPE having a MI of about 2 g/10 min. In another embodiment, the film comprises LDPE having a MI of about 0.2 g/10 min. In illustrative embodiments, the film comprises LDPE having a density of about 0.91 g/cm$^3$ to about 0.93 g/cm$^3$. In another embodiment, the film comprises LDPE having a density of about 0.92 g/cm$^3$.

HDPE. In illustrative embodiments, the multilayer film includes at a layer comprised of high density polyethylene, referred to herein as HDPE. In another embodiment, the high density polyethylene is a product of reacting ethylene by a means to form a product exhibiting very little short chain or long chain branching so that the polyethylene has a highly crystalline structure.

In illustrative embodiments, the high density polyethylene is a homo-polymeric high density polyethylene with a mono-modal MWD. The homo-polymeric high density polyethylene is a product of reacting ethylene such that the product has substantially no branching. In one embodiment, the homo-polymeric high density polyethylene has a MI of about 1 g/10 min to about 9 g/10 min and a density of about 0.935 g/cm$^3$ to about 0.96 g/cm$^3$.

EAC. As used herein, the term ethylene acrylate copolymers (EAC) include polymers with various molecular weights, densities, and tacticities synthesized from ethylene and acrylate monomers. Included within the scope of this disclosure are copolymers such as ethylene methyl acrylate (EMA), ethylene ethyl acrylate (EEA), ethylene butyl acrylate (EBA) and ethylene vinyl acetate (EVA). In one embodiment, the EAC are random copolymers. In another embodiment, the EAC is a block copolymer. In yet another embodiment, the EAC is phase separated, that is, the copolymer is polymerized in a manner such that the blocks are immiscible. Accordingly, the EAC of the present disclosure includes polymers that have ordered microstructures. Also included within the scope of this disclosure are EAC polymers exhibiting ordered morphologies such as spheres, cylinders, and lamellae, ordered bicontinuous double-diamond, ordered tricontinuous double-diamond or perforated-lamellar morphologies.

In illustrative embodiments, the film includes an ethylene-vinyl acetate (EVA) copolymer containing substantial long chain branching. In one embodiment, the EVA is the type that is made using a high pressure process. For example, the EVA may be manufactured through a free radical polymerization reaction between ethylene and vinyl acetate. In one embodiment, this polymerization may be performed in conventional stirred autoclave or tubular reactors at high pressure (in this context, greater than about 20,000 psi) and at high temperatures (in this context, from about 200-320° C.). In another embodiment, the molecular weight of the EVA copolymers is controlled by the addition of chain terminators, such as propylene or isobutylene. In another embodiment, the type and level of branching of an EVA copolymer may be similar to that observed in LDPE.

In another embodiment, from about 5 to about 50 weight percent (based on the total weight of the final EVA copolymer) vinyl acetate is copolymerized with ethylene. In yet another embodiment, the EVA copolymers have vinyl acetate content from about 2% to about 9%, based on the total weight of the final EVA copolymer. In one embodiment, EVA copolymer comprises from about 5% to about 15% by weight copolymerized vinyl acetate and has a density from about 0.88 g/cm$^3$ to 0.912 g/cm$^3$ and melt indexes from about 0.5 to 10 g/10 min.

In illustrative embodiments, the film comprises EAC having a MI of about 0.1 to about 20 g/10 min. In one embodiment, the film comprises EAC having a MI of about 0.5 to about 8 g/10 min. In one embodiment, the film comprises EAC having a MI of about 0.5 to about 0.8 g/10 min. In another embodiment, the film comprises EAC having a MI of about 0.65 g/10 min. In illustrative embodiments, the film comprises EAC having a density of about 0.91 g/cm$^3$ to about 0.93 g/cm$^3$. In one embodiment, the film comprises EAC having a density of about 0.920 g/cm$^3$ to about 0.925 g/cm$^3$. In another embodiment, the film comprises EAC having a density of about 0.92 g/cm$^3$. In another embodiment, the EAC has a density of about 0.945 g/cm$^3$, a MI of about 10.0 g/10 m and contains about 24% of methyl acrylate co-monomer.

In illustrative embodiments, the film includes at least one layer containing an EMA copolymer. In one embodiment, the EMA copolymer has a MI from about 3 to about 7. In another embodiment, the EMA copolymer has a density in the range of about 0.93 g/cm$^3$ to about 0.96 g/cm$^3$. In one embodiment, the EMA copolymer includes about 15% to about 35% methyl acrylate units and from about 65% to about 85% ethylene units. In one embodiment, the EMA copolymer includes about 24% methyl acrylate units and about 76% ethylene units.

EP copolymer. As used herein, the term ethylene propylene copolymer (EP copolymer) includes polymers with various molecular weights, densities, and tacticities synthesized from ethylene and propylene monomers in various ratios. For example, the term EP copolymer includes polymers comprised predominantly of ethylene units and polymers predominantly of propylene units. For example, EP copolymers within the scope of this disclosure may include from about 1% to about 99% ethylene monomer units and from about 1% to about 99% propylene monomer units.

In illustrative embodiments, the film comprises EP copolymer having a MI of about 0.1 to about 20 g/10 min. In one embodiment, the film comprises EP copolymer having a MI of about 4 to about 14 g/10 min. In one embodiment, the film comprises EP copolymer having a MI of about 6 to about 8 g/10 min. In illustrative embodiments, the film comprises EP copolymer having a density of about 0.88 g/cm$^3$ to about 0.92 g/cm$^3$. In one embodiment, the film comprises EP copolymer having a density of about 0.89 g/cm$^3$ to about 0.91 g/cm$^3$. In another embodiment, the film comprises EP copolymer having a density of about 0.900 g/cm$^3$ to about 0.902 g/cm$^3$. In illustrative embodiments, the film comprises EP copolymers comprising a random copolymer structure with from about 0.1% to about 8% ethylene. In one embodiment, the EP copolymer comprises from about 3% to about 5% ethylene in a random copolymer structure.

PA. In illustrative embodiments, one or more layers may comprise a polyamide (PA).

PP. In illustrative embodiments, one or more layers may comprise a polypropylene. As used herein, the term polypropylene (PP) includes polymers with various molecular weights, densities, and tacticities synthesized from propylene monomers. The term PP is intended to include polymers which are homopolymers of propylene or copolymers of propylene or other lower or higher alpha olefins, such as ethylene. The term PP, within the scope of this disclosure, includes PP characterized as soft PP. In illustrative embodiments, the PP is a polypropylene homopolymer has a density of about 0.9 g/cm$^3$, and an MI of about 12 g/10 min.

PIB. In illustrative embodiments, one or more layers may include a poly-isobutylene (PIB). According to one embodiment, the PIB may have been produced by polymerization of about 98% of isobutylene with about 2% of isoprene. According to another embodiment, the PIB may have been produced by polymerization of 2-methyl-1-propene. In illustrative embodiment, the PIB may have a number average molecular weight in the range from about 1,000-3,000 g/mol as measured by vapor phase osmometry. In another embodiment, the PIB may have a number average molecular weight in the range from about 1200-1800 g/mol as measured by vapor phase osmometry.

SBC. As used herein, the term styrenic block copolymer (SBC) includes polymers having styrene polymerized with at least one copolymer in a manner such that a block copolymer results. One of ordinary skill in the art will appreciate that a block copolymer is substantially different than a random copolymer due to the blocked molecular structure. Within the scope of block copolymer are copolymers of styrene with one of or a combination of butadiene, butylene, ethylene, isoprene. One aspect of a SBC polymer is that it may exhibit micro- or nano-scale phase separation. For example, an SBC may form a periodic nanostructures. In one embodiment, SBC has a density of about 0.9 g/cm$^3$, and a MI of from about 2 g/10 min and about 25 g/10 min.

While not being limited to a particular theory, the polymers herein may be blended in various ratios to obtain a polymeric blend having the desired properties for a given layer. The polymer blends may be formed by any convenient method, including dry blending the individual components and subsequently melt mixing, either directly in the extruder used to make the film, or by pre-melt mixing in separate extruder before making the film. The polymer blends may also be prepared by dual polymerization techniques, or by melt conveying the desired amount of a first polymer directly into a molten stream of second polymer from a polymerization reactor, prior to pelletization of the polymer blend. The polymer blends can also be made by dry blending discrete polymers having the specified properties in appropriate weight ratios, as described herein.

In illustrative embodiments, one or more layers may include a blend of a cPE and a LDPE. Reference is made to U.S. Pat. No. 7,172,815, which is hereby incorporated by reference herein, for disclosure relating to blends of cPE and LDPE. In one embodiment, a blend comprises LDPE and cPE. In one aspect, the proportion of cPE:LDPE in the polymer blend is dependent upon the molecular weight of the LDPE. In one embodiment, the cPE:LDPE ratio is from about 5:1 to about 33:1. In another embodiment, the cPE:LDPE ratio is from about 7:1 to about 25:1. For a LDPE with a MI from about 0.1 to about 1 g/10 min, the cPE:LDPE ratio is from about 16:1 to about 33:1. In one embodiment, for a LDPE having a MI of greater than about 1 g/10 min to about 2 g/10 min, the cPE:LDPE ratio is from about 7:1 to about 24:1. In another embodiment, for a LDPE having a MI of greater than about 1 g/10 min to about 2 g/10 min, the cPE:LDPE ratio is from about 7:1 to about 16:1. In one embodiment, for a LDPE having a MI of greater than about 2 g/10 min to about 20 g/10 min, the cPE:LDPE ratio is from about 4.5:1 to about 16:1. In another embodiment, for a LDPE having a MI of greater than about 2 g/10 min to about 20 g/10 min, the cPE:LDPE ratio is from about 4.5:1 to about 7.5:1.

Referring again to FIGS. 4A-4C, peelable co-extruded multilayer film 14/14'/14" comprises skin layer 16, core 18/18'/18", and exterior layer 20, where core 18/18'/18" is interposed and in contact with skin layer 16 and exterior layer 20. In a first illustrative embodiment shown in FIG. 4A, core 18 comprises a first polymer layer 181, a second polymer layer 182, a third polymer layer 183, a fourth polymer layer, and a fifth polymer layer 185. In a second illustrative embodiment shown in FIG. 4B, core 18' comprises a first polymer layer 181', a second polymer layer 182', and a third polymer layer 183'. In a third illustrative embodiment shown in FIG. 4C, core 18" comprises a first (single) polymer layer 181".

Skin layer 16. Again, without wishing to be bound by theory, it is believed that the combination of thickness, polymer melt index, and polyolefin content of skin layer 16, in combination with suitable slip and anti-block components, contribute substantially to the peelability characteristics described herein.

In illustrative embodiments, skin layer 16 is thin, e.g., about 10% of the total thickness of peelable film 14/14'/14". As such, one aspect of the present disclosure is that interposed skin layer 16 represents a minor amount (e.g., as little as about 5% to as much as about 20%) of the total thickness of co-extruded multilayer film 14/14'/14". In an embodiment, the skin layer can be about 5%, 6%, 7%, 8%, 9%, 10%, 11%, 12%, 13%, 14%, 15%, 16%, 17%, 18%, 19%, or 20% of the total thickness of co-extruded multilayer film 14/14'/14". However, while the dimensional contribution of skin layer 16 may be small, the consequence of its inclusion leads to a significant improvement in the peelability properties of multilayer film 14/14'/14". In this respect, interposed skin layer 16's thickness contributes only slightly to the total thickness of the film (preferably 3 to 3.5 mil although other thicknesses are possible), but substantially to the film's overall properties.

In illustrative embodiments, skin layer 16 comprises a polymer, e.g., LDPE, as a base sealant having a MI of about 6. It is anticipated that MI may vary over a range, e.g., about 3 to about 10, and still impart desirable peel characteristics to co-extruded multilayer film 14/14'/14". Specifically, the MI can be about 3, about 4, about 5, about 6, about 7, about 8, about 9, and about 10. Other exemplary polymers believed to have MI in this range include, but are not limited to, PA, VLDPE, LLDPE, HDPE, EVA copolymers, EP copolymers, PP homopolymers and copolymers, as well as combinations and mixtures thereof.

In illustrative embodiments, skin layer 16 comprises a poly-alpha olefin, e.g., polybutene-1, as a peel agent present in about 20% to about 80% by weight, about 30% to about 50% by weight, about 35% to about 45% by weight, or about 40% by weight. It is anticipated that other poly-alpha olefinic peel agents, such as poly(3-methyl-1-butene), polypentene-1, polyhexene-1, poly(3-methyl-1-pentene), poly(4-methyl-1-pentene), poly(3-methyl-1-hexene), poly(1-octene), poly(1-decene), and like polymers, present in about 40% by weight, may impart desirable peel characteristics to co-extruded multilayer film 14.

Exterior layer 20. Exterior layer 20 comprises one or more polymers such as, for example, polyethylene, polypropylene, polybutylene, and like polymers as well as copolymers, combinations, and mixtures thereof, cPE copolymers, PA, VLDPE, LDPE, LLDPE, HDPE, PIB, SBC, EAC, EMA copolymers, EEA copolymers, EBA copolymers, EVA copolymers, EP copolymers, PP homopolymers and copolymers, as well as combinations and mixtures thereof. In one embodiment, exterior layer 20 comprises cPE. In another embodiment, exterior layer 20 comprises PP. In yet another embodiment, exterior layer 20 comprises HDPE. In one embodiment, exterior layer 20 comprises LDPE. In one embodiment, exterior layer comprises LLDPE. In one embodiment, exterior layer 20 comprises a blend of LLDPE and one or more polymers selected from the group consisting of cPE, PP, HDPE, EP copolymer and LDPE. In illustrative embodiments, exterior layer 20 may include any of several non-cling or antiblock additives to improve the non-cling characteristics of the layer. Such additives include silicas, talcs, diatomaceous earth, silicates, lubricants, etc.

Core 18. Referring now to FIG. 4A, core 18 comprises a first polymer layer 181, a second polymer layer 182, a third polymer layer 183, a fourth polymer layer, and a fifth polymer layer 185, each of which layer comprises one or more independently selected polymers such as, for example, polyethylene, polypropylene, polybutylene, and like polymers as well as copolymers, combinations, and mixtures thereof, cPE copolymers, PA, VLDPE, LDPE, LLDPE, HDPE, PIB, SBC, EAC, EMA copolymers, EEA copolymers, EBA copolymers, EVA copolymers, EP copolymers, PP homopolymers and copolymers, as well as combinations and mixtures thereof. In one embodiment, first polymer layer 181 comprises LDPE. In another embodiment, second polymer layer 182 comprises LLDPE. In yet another embodiment, third polymer layer 183 comprises a PA. In another embodiment, fourth polymer layer 184 comprises LLDPE. In another embodiment, fifth polymer layer 185 comprises a mixture or a blend of LDPE and LLDPE. In yet another embodiment, first polymer layer 181 comprises LDPE, second polymer layer 182 comprises LLDPE, third polymer layer 183 comprises a PA, fourth polymer layer 184 comprises LLDPE, and fifth polymer layer 185 comprises a mixture or a blend of LDPE and LLDPE.

Core 18'. Referring now to FIG. 4B, core 18' comprises a first polymer layer 181', a second polymer layer 182', and a third polymer layer 183', each of which layer comprises one or more independently selected polymers such as, for example, polyethylene, polypropylene, polybutylene, and like polymers as well as copolymers, combinations, and mixtures thereof, cPE copolymers, PA, VLDPE, LDPE, LLDPE, HDPE, PIB, SBC, EAC, EMA copolymers, EEA copolymers, EBA copolymers, EVA copolymers, EP copolymers, PP homopolymers and copolymers, as well as combinations and mixtures thereof. In one embodiment, first polymer layer 181' comprises LDPE. In another embodiment, second polymer layer 182' comprises a PA. In yet another embodiment, third polymer layer 183' comprises a mixture or a blend of LDPE and LLDPE. In yet another embodiment, first polymer layer 181' comprises LDPE, second polymer layer 182' comprises a PA, and third polymer layer 183' comprises a mixture or a blend of LDPE and LLDPE.

Core 18". Referring now to FIG. 4C, core 18" comprises a first (single) polymer layer 181", which layer includes one or more polymers such as, for example, polyethylene, polypropylene, polybutylene, and like polymers as well as copolymers, combinations, and mixtures thereof, cPE copolymers, PA, VLDPE, LDPE, LLDPE, HDPE, PIB, SBC, EAC, EMA copolymers, EEA copolymers, EBA copolymers, EVA copolymers, EP copolymers, PP homopolymers and copolymers, as well as combinations and mixtures thereof. In one embodiment, first polymer layer 181" comprises LDPE. In another embodiment, first polymer layer 181" comprises a PA. In yet another embodiment, first polymer layer 181" comprises a mixture or a blend of LDPE and LLDPE. Embodiments of the peelable film disclosed herein have at least one core layer. Embodiments of the peelable film disclosed herein can have 1, 2, 3, 4, 5, 6, or more core layers.

Figure 5:
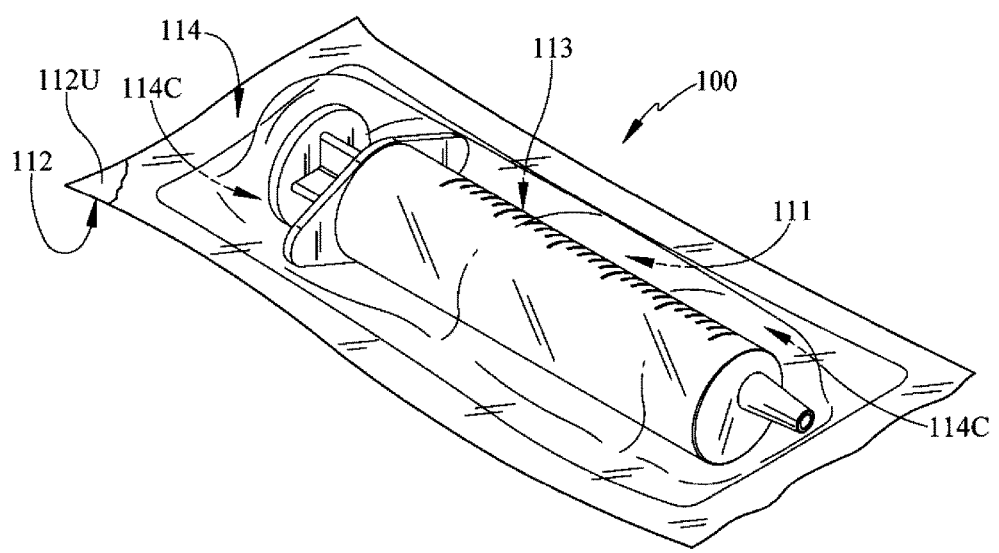
FIG. 5 is a top perspective view of a package in accordance with a second embodiment of the present disclosure formed to include an article-receiving space containing a syringe, with a portion broken away to reveal an upwardly facing uncoated sealant side of a paper substrate.
Figure 6:
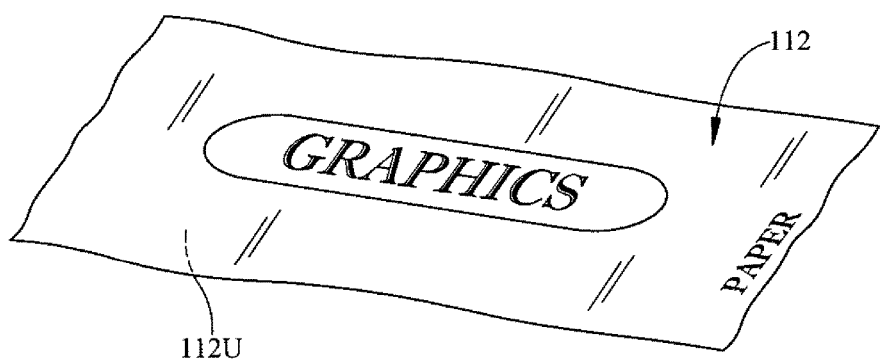
FIG. 6 is a bottom perspective view of the package of FIG. 5 showing a graphics design printed on an exterior surface of the paper substrate included in the package.

A package 100 in accordance with a second embodiment of the present disclosure is shown in FIGS. 5 and 6 and includes a substrate topweb 112 made of paper having an uncoated sealant side 112U, a multilayer film 114 (forming web) comprising a skin layer 16 adapted to be bonded to uncoated sealant side 112U of paper 112, and a syringe 113 located in an article-storage channel 114C formed in film 114 to define an article-receiving space 111 provided between film 114 and uncoated sealant side 112U of paper 112. To access syringe 113, a technician can peel back paper 112 as suggested in FIG. 12 to release uncoated sealant side 112U of paper 112 from skin layer 16 of film 114 without separating paper fibers from uncoated sealant side 112U of paper 112 and discharging those paper fibers into article-receiving space 111 and article-storage channel 114C so that no fiber tear is present.

Figure 7:
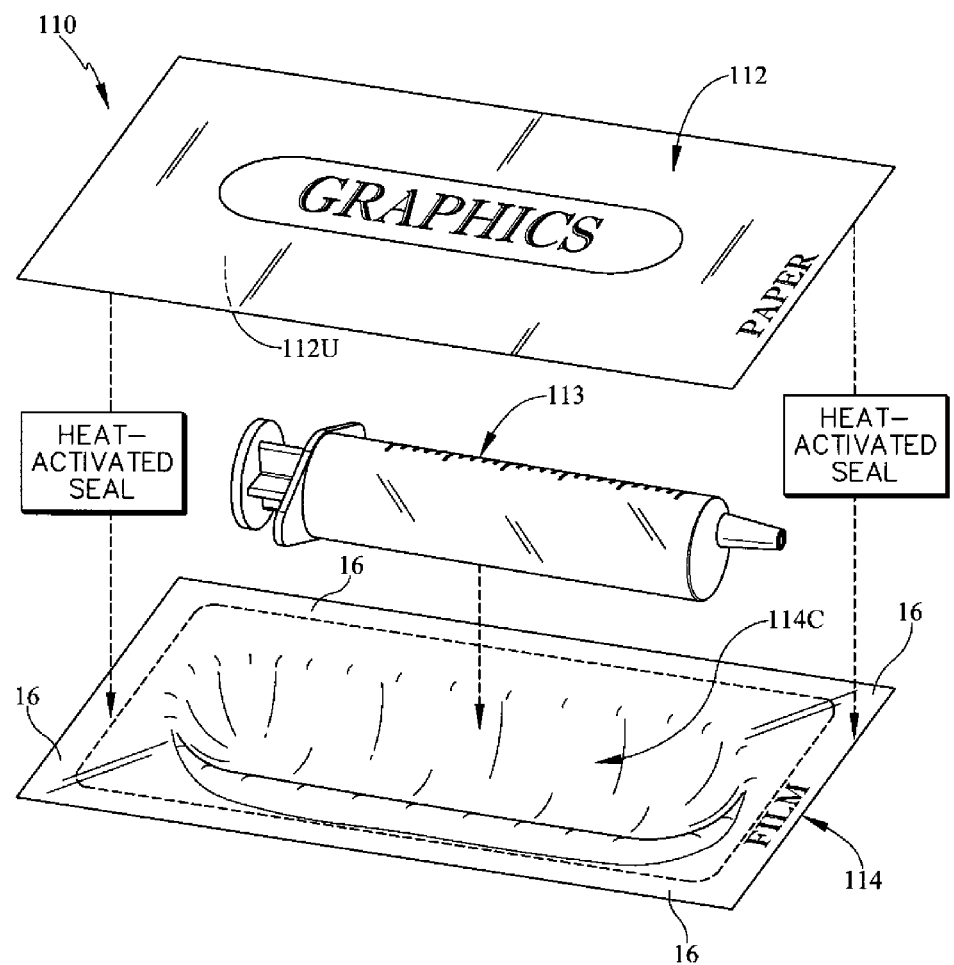
FIG. 7 is an exploded perspective assembly view showing that the package of FIGS. 5 and 6 includes (from top to bottom) a substrate (topweb) made of paper bearing printed graphics material and including a downwardly facing uncoated sealant side, a syringe, and a film (forming web) formed to include an article-storage channel sized to receive the syringe and a skin layer facing upwardly toward the uncoated sealant side of the paper and suggesting that the skin layer mates with the uncoated sealant side of the paper by means of a heat-activated seal to bond the film to the uncoated sealant side of the paper while the syringe is received in the article-storage channel formed in the film.
Figure 12:
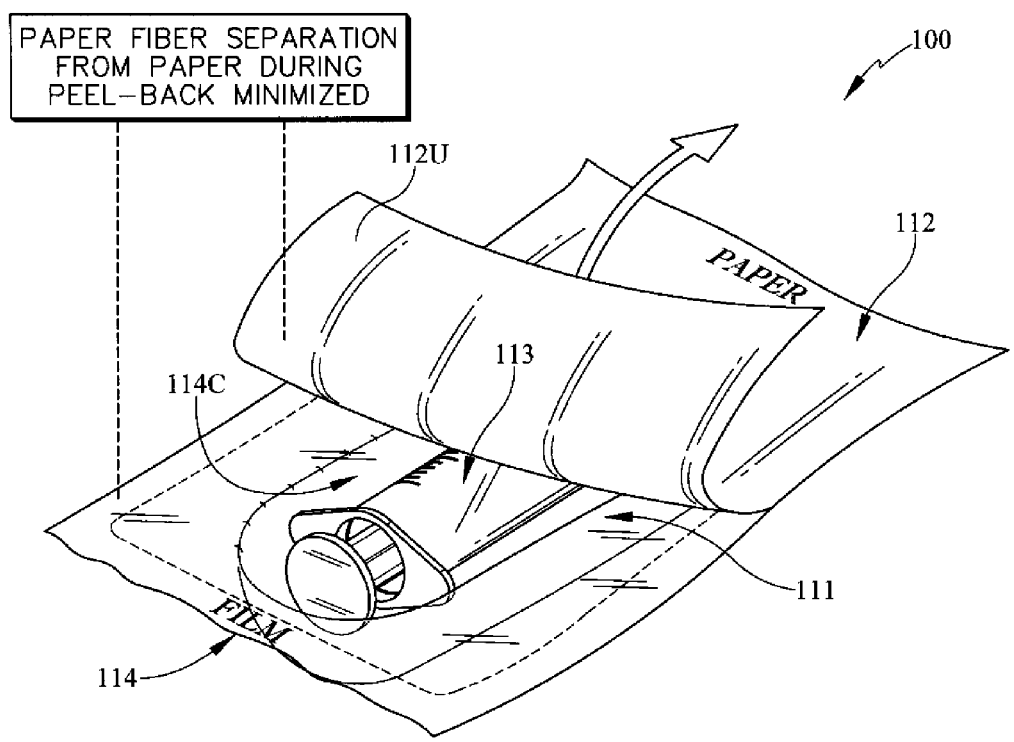
FIG. 12 is an enlarged perspective view of the package of FIGS. 5-7 showing that an external peeling force is being applied, for example, to the paper to release the skin layer of the multilayer film from a bonded connection to the uncoated sealant side of the paper without separating paper fibers from the uncoated sealant side of the paper and discharging paper fibers into an article-receiving space provided between the film and the uncoated sealant side of the paper and article-storage channel formed in the film so that the uncoated paper remains substantially intact during separation of the film from the uncoated paper.

Film 114 is bonded to uncoated sealant side 112U of paper 112 or other suitable substrate or topweb using heat as suggested in FIG. 7 to trap an article such as syringe 113 in an article-receiving space 111 formed between film 114 and uncoated sealant side 112U of paper 112. Skin layer 16 of film 114 bonds directly to uncoated sealant side 112U of paper 112 to provide a hermetic seal therebetween and yet skin layer 16 separates very easily from uncoated sealant side 112U of paper 112 when paper 112 is peeled back as suggested in FIG. 12. Film 114 is a forming web that is heat-sealed to the sealant side 112U of uncoated paper topweb 112. Package 100 can be sterilized by exposure to radiation, gas, or other means to cause syringe 113 stored in package 10 also to be sterilized. A paper can be, but not limited to, Arjo-Wiggins D560.

Skin layer 16 of film 114 is a composition that releases easily from uncoated sealant side 112U of paper 112 in an unexpected manner to break the hermetic seal between uncoated sealant side 112U of paper 112 and film 114 to access syringe 113 without separating paper fibers from uncoated sealant side 112U of paper 112 and discharging paper fibers into article-receiving space 111 where such fibers may contact syringe 113 as package 100 is being opened. Skin layer 16 is one of, for example, many layers included in a co-extruded multilayer film 114. Examples of illustrative films in accordance with the present disclosure are include in FIGS. 4A-4C. It is therefore unnecessary to use an expensive coated paper as a substrate owing to the adhesion properties of skin layer 16 in film 114. Costly coatings are often applied to sealant sides of paper substrates to cause those paper substrates to adhere to a film web with a specific seal strength and to cause those paper substrates not to shed any paper fibers during separation of the film from the paper substrate.

Film 114 is a blown co-extruded film, illustratively a multilayer forming web with a skin layer 16 that is capable of forming a peelable seal to an uncoated sealant side 112U of paper topweb 112. The seal peels cleanly without pulling paper fibers from the uncoated sealant side 112U of paper 112 during seal opening in accordance with the present disclosure.

An illustrative process for forming package 100 is shown diagrammatically in FIGS. 8-11. Film 114 is moved onto a heatable vacuum bed 40 in a thermoformer apparatus as suggested in FIG. 8 so that an exterior layer of film 114 mates with heatable vacuum bed 40 and skin layer 16 faces away from vacuum bed 40. Bed 40 is heated and a vacuum generated by vacuum source 42 to deform film 114 to assume the molded shape shown in FIG. 9. Once molded, film 114 is formed to include article-storage channels 114C as suggested in FIG. 9 and a syringe 113 can be placed in one of these channels 114C before uncoated sealant side 112U of paper 112 is mated to skin layer 16 of film 114.

A heat-activated seal is established between mating portions of uncoated sealant side 112U of paper 112 and skin layer 16 of multilayer film 114 as suggested in FIG. 10. It is within the scope of the is disclosure to form two packages 100 as shown in FIG. 11 connected to one another by any suitable (frangible) means.

Embodiments of a multilayer peelable film as described herein provide an easy peel system bonded to a substrate. The substrate can be uncoated paper. The uncoated paper can be, but not limited to, Arjo Wiggins DS60. An easy peel system comprising a multilayer peelable film as described herein does not exhibit paper fiber tears when the film is unmated from a paper substrate (e.g., paper). A multilayer peelable film in a system as described herein can have a peel seal strength of about 0.5 to about 3.0 lbs/in, about 0.5 to about 2.5 lbs/in, 0.5 to about 2.0 lbs/in, 0.5 to about 1.5 lbs/in, 0.5 to about 1.0 lbs/in, 1.0 to about 3.0 lbs/in, 1.0 to about 2.5 lbs/in, 1.0 to about 2.0 lbs/in, 1.0 to about 1.5 lbs/in, 1.5 to about 3.0 lbs/in, 1.5 to about 2.5 lbs/in, 1.5 to about 2.0 lbs/in, and will not tear paper fibers when unmated from a paper substrate (e.g., a package). In an embodiment, a multilayer peelable film can have a peel seal strength of about 0.5 lbs/in, 1.0 lbs/in, 1.1 lbs/in, 1.2 lbs/in, 1.25 lbs/in, 1.3 lbs/in, 1.4 lbs/in, 1.5 lbs/in, 1.6 lbs/in, 2.0 lbs/in, 2.5 lbs/in, or 3.0 lbs/in, and will not tear paper fibers when unmated from a paper substrate (e.g., a package).

EXAMPLE I

Co-extruded Multilayer Peelable Film

A multilayer peelable sealant film in accordance with FIG. 4A was prepared using a conventional blown film co-extrusion process. The formulation of the co-extruded multilayer peelable film is shown in Table 1.

TABLE 1

| | Co-extruded Multilayer Peelable Film Formulation | | | | | |
|---|---|---|---|---|---|---|
| | Layer Information | | Approximate Resin | | | |
| # | Sub-layer Type | Approximate Sub-layer Percentage | Composition in Percentage | Resin Supplier | Resin Number | Resin Type |
| Layer formulation for multilayer peelable film shown in FIG. 4A | Exterior Layer | 30% | 67% | Nova | PF0118C | LLDPE |
| | | | 30% | Exxon | LD105.30 | LDPE |
| | | | 2% | Ampacet | 10063 | 20% Dia. AB |
| | | | 1% | Ampacet | 10090 | 5% Eru. Slip |
| | Fifth Polymer Layer | 14% | 70% | Nova | PF0118C | LLDPE |
| | | | 30% | Exxon | LD105.30 | LDPE |
| | Fourth Polymer Layer | 8% | 15% | DuPont | 41E710 | LLDPE |
| | | | 85% | Nova | FP120C | LLDPE |
| | Third Polymer Layer | 20% | 96.5% | BASF | C33LN01 | Polyamide |
| | | | 3.5% | BASF | FMB2052 | Polyamide |
| | Second Polymer Layer | 8% | 15% | DuPont | 41E710 | LLDPE |
| | | | 85% | Nova | FP120C | LLDPE |
| | First Polymer Layer | 10% | 100% | Exxon | LD105.30 | LDPE |
| | Skin Layer | 10% | 57% | Equistar | NA334000 | LDPE |
| | | | 40% | Basell | PB1600M | Polybutene-1 |
| | | | 1% | Ampacet | 10090 | 5% Eru. Slip |
| | | | 2% | Ampacet | 10063 | 20% Dia. AB |

EXAMPLE II

Co-extruded Multilayer Peelable Film

A multilayer peelable sealant film in accordance with FIG. 4A was prepared using a conventional blown film co-extrusion process. The formulation of the co-extruded multilayer peelable film is shown in Table 2.

TABLE 2

Co-extruded Multilayer Peelable Film Formulation

| Sub-layer Type | Approximate Sub-layer Percentage | RESIN Number | Approximate Resin Composition in Percentage | Resin Supplier | Resin Name | Resin Type |
|---|---|---|---|---|---|---|
| Exterior Layer | 31.0% | PF0118C | 67.00% | Nova | butene | LLDPE |
| | | LD105.30 | 30.00% | Exxon | | LDPE |
| | | 10063 | 2.00% | Ampacet | | 20% Dia. AB |
| | | 10090 | 1.00% | Ampacet | | 5% Eru. Slip |
| Fifth Polymer Layer | 12.0% | 41E710 | 15.00% | DuPont | Bynel | Tie Concentrate |
| | | 2056G | 85.00% | Dow | Dowlex | OCT LLDPE |
| Fourth Polymer Layer | 10.0% | C33LN01 | 96.50% | #N/A | #N/A | #N/A |
| | | FMB2052 | 3.50% | #N/A | #N/A | #N/A |
| Third Polymer Layer | 12.0% | 41E710 | 15.00% | DuPont | Bynel | Tie Concentrate |
| | | FP120C | 85.00% | #N/A | #N/A | #N/A |
| Second Polymer Layer | 10.0% | C33LN01 | 15.00% | #N/A | #N/A | #N/A |
| | | FMB2052 | 85.00% | #N/A | #N/A | #N/A |
| First Polymer Layer | 15.0% | LD105.30 | 85.00% | Exxon | | LDPE |
| | | 41E710 | 15.00% | DuPont | Bynel | Tie Concentrate |
| Skin Layer | 10.0% | NA334000 | 57.00% | Equistar | Petrothene 0 | LDPE |
| | | PB1600M | 40.00% | Basell | | PB |
| | | 10090 | 1.00% | Ampacet | | 5% Eru. Slip |
| | | 10063 | 2.00% | Ampacet | | 20% Dia. AB |

EXAMPLE III

Multilayer peelable sealant films were prepared using a conventional blown film co-extrusion process. Seal strength of the multilayer peelable sealant films comprising a skin layer was tested. The skin layer comprised polyethylene and 40% polybutene-1. Additionally, the skin layer was 10% of the film, and the film was 3.5 mil thick. The skin layer was mated to uncoated paper (Arjo Wiggins DS60). The "green" samples were sealed and pulled right after the seal was made. A ten second cool down followed before measuring the strength. The "aged" samples were sealed and allowed to stay sealed 14 days before pulling apart. The tests were conducted with an Enepay heat seal tester (Magma) at 60 psi and a one second dwell. The tester makes the seal, pulls the film from the paper, and then measures the peel force. The data were collected and are in Table 3.

TABLE 3

The average seal strength of green versus aged packages.

| | Average Heat Seal Strength (g/in) | |
|---|---|---|
| Temp (° F.) | Green | Aged |
| 230 | 43 | 17 |
| 240 | 308 | 411 |
| 250 | 461 | 506 |
| 260 | 511 | 411 |
| 270 | 595 | 420 |
| 280 | 615 | 419 |
| 290 | 628 | 424 |
| 300 | 659 | 439 |
| 310 | 634 | 432 |
| 320 | 601 | 444 |

EXAMPLE IV

Multilayer peelable sealant films were prepared using a conventional blown film co-extrusion process. The multilayer peelable sealant films were tested with different skin layers for heat seal strength (g/in) over various temperatures (° F.). Packages comprising a multilayer peelable sealant film were produced on a Multivac R145. The packages were aged 3 to 5 days. Then 1 inch wide specimens were taken from each package and then tested on an Instron tensile tester for peel strength.

Film A had a skin layer that was 10% of the total film, which was 3.5 mil thick, and comprised 40% polybutene-1. Film B had a skin layer that was 15% of the total film, which was 1.3 mil thick, and comprised 40% polybutene-1. Film C had a skin layer that was 10% of the total film, which was 1.3 mil thick, and comprised 45% polybutene-1. Film D had a skin layer that was 10% of the total film, which was 3.0 mil thick, and comprised 35% polybutene-1. Packages

TABLE 4

The heat seal strength of formulations of a multilayer peelable sealant film over various temperatures.

| Temp (° F.) | Average Heat Seal Strength (g/in) | | | |
|---|---|---|---|---|
| | A | B | C | D |
| 240 | 411 | 170 | 145 | 117 |
| 250 | 506 | 381 | 271 | 383 |
| 260 | 411 | 443 | 336 | 476 |
| 270 | 420 | 400 | 318 | 443 |
| 280 | 419 | 391 | 304 | 426 |
| 290 | 424 | 414 | 321 | 420 |

EXAMPLE V

Multilayer peelable sealant films were prepared using a conventional blown film co-extrusion process. The multilayer peelable sealant films were tested with different skin layers for heat seal strength (On) over various temperatures (° F.). Packages comprising a multilayer peelable sealant film were produced on a Multivac R145. The packages were aged 3 to 5 days. Then 1 inch wide specimens were taken from each package and then tested on an Instron tensile tester for peel strength.

These films were tested with different formulations of skin layers for heat seal strength (On) over various temperatures (° F.). Film A had a skin layer that was 10% of the total film and comprised 45% polybutene-1. Film B had a skin layer that was 10% of the total film and comprised 35% polybutene-1. Film C had a skin layer that was 10% of the total film and comprised 40% polybutene-1.

TABLE 5

The heat seal strength of formulations of a multilayer peelable sealant film over various temperatures.

| Temp (° F.) | Average Heat Seal Strength (g/in) | | |
|---|---|---|---|
| | A | B | C |
| 240 | 165 | 187 | |
| 250 | 242 | 349 | 289 |
| 260 | 290 | 411 | 320 |
| 270 | 258 | 397 | 291 |
| 280 | 268 | | |
| 290 | 272 | | |

The invention claimed is:

1. A multilayer peelable film comprising an exterior layer, at least one core layer, and a skin layer,
    wherein the skin layer comprises about 5% to about 20% of a thickness of the film,
    wherein the skin layer consists of low-density polyethylene (LDPE), poly-alpha olefin, a slip component, and an antiblock component,
    wherein about 40% of the skin layer is the poly-alpha olefin,
    wherein 57% of the skin layer is the low-density polyethylene (LDPE),
    wherein the LDPE has a melt index of 6 g/10 min, and
    wherein the poly-alpha olefin is polybutene-1.

2. The multilayer peelable film of claim 1, wherein the poly-alpha olefin has a melt index of about 1.

3. The multilayer peelable film of claim 1, wherein the skin layer comprises about 10% of the total film.

4. The multilayer peelable film of claim 1, wherein the total film is 3 to 3.5 mil thick.

5. The multilayer peelable film of claim 1, wherein the film has a peel seal strength of about 0.5 to about 3 pounds per inch.

6. The multilayer peelable film of claim 1, wherein the LDPE is an ethylene homopolymer.

* * * * *